United States Patent
Boschetti et al.

(10) Patent No.: US 7,833,625 B2
(45) Date of Patent: Nov. 16, 2010

(54) MATERIALS, METHODS AND SYSTEMS FOR SEPARATING AND IDENTIFYING PROTEINS FROM MIXTURES

(75) Inventors: Egisto Boschetti, Croissy sur Seine (FR); Pier Giorgio Righetti, Milan (IT)

(73) Assignee: Bio-Rad Laboratories, Inc., Hercules, CA (US)

( * ) Notice: Subject to any disclaimer, the term of this patent is extended or adjusted under 35 U.S.C. 154(b) by 1588 days.

(21) Appl. No.: 11/074,591

(22) Filed: Mar. 8, 2005

(65) Prior Publication Data

US 2005/0227001 A1    Oct. 13, 2005

Related U.S. Application Data

(60) Provisional application No. 60/553,605, filed on Mar. 17, 2004, provisional application No. 60/553,561, filed on Mar. 17, 2004, provisional application No. 60/566,872, filed on Apr. 30, 2004.

(51) Int. Cl.
*B32B 5/16* (2006.01)

(52) U.S. Cl. ............... 428/403; 428/404; 428/405; 428/406; 428/407; 502/400; 210/656

(58) Field of Classification Search ......... 428/403–407, 428/474.4; 502/400; 210/656
See application file for complete search history.

(56) References Cited

U.S. PATENT DOCUMENTS

| | | | |
|---|---|---|---|
| 4,971,670 A | | 11/1990 | Faupel et al. |
| 5,393,430 A | * | 2/1995 | Girot et al. ............ 210/635 |
| 5,445,732 A | * | 8/1995 | Girot et al. ............ 210/198.2 |
| 5,470,463 A | * | 11/1995 | Girot et al. ............ 210/198.2 |
| 5,470,916 A | * | 11/1995 | Righetti et al. ............ 525/296 |
| 6,355,709 B1 | | 3/2002 | Madabhushi et al. |
| 6,613,234 B2 | * | 9/2003 | Voute et al. ............ 210/656 |
| 2002/0005383 A1 | | 1/2002 | Voute et al. |
| 2003/0042203 A1 | | 3/2003 | Wormsbecher |

FOREIGN PATENT DOCUMENTS

WO    WO 03101591    12/2003

OTHER PUBLICATIONS

Marina Cretich et al., "Separation of proteins in a multicompartment electrolyzer with chambers defined by a bed of gel beads", Electrophoresis 2003, 24, pp. 577-581.
Pier Giorgio Righetti et al., "Macroreticulate buffers: a novel approach to pH control in living systems", Journal of Biotechnology, 17, 1991, pp. 169-176.
Marcella Chiari et al., "Physico-chemical properties of amphoteric, isoelectric, macroreticulate buffers", Journal of Biochemical and Biophysical Methods, 23, (1991) pp. 115-130.
Raffaello Pompei et al., "Culture of Eukaryotic Cells with Macro-reticulate Buffers: Fermentation of Cellulolytic Fungi", BioFeedback, Circle Reader Service No. 116, vol. 11, No. 6 (1991) pp. 703-706.
João Meireles Ribeiro et al., "An Algorithm for the Computer Calculation of the Coefficients of a Polynomial That Allows Determination of Isoelectric Points of Proteins and Other Macromolecules", Comput. Biol. Med. vol. 20, No. 4, pp. 235-242, 1990.
João Meireles Ribeiro et al., "A Program to Calculate the Isoelectric Point of Macromolecules", Comput. Biol. Med. vol. 21, No. 3, pp. 131-141, 1991.
Antonio Sillero et al., "Isoelectric Points of Proteins: Theoretical Determination", Analytical Biochemistry, 179, pp. 319-325 (1989).

* cited by examiner

*Primary Examiner*—Leszek Kiliman
(74) *Attorney, Agent, or Firm*—Morgan, Lewis & Bockius, LLP (57) ABSTRACT

Materials, apparatuses, methods, and systems for isolating and identifying mixture components on the basis of isoelectric point ("pI"). In one aspect, the materials are particles adapted to have a predetermined isoelectric point. The particles include a porous body into which a plurality of cavities extend. A substance of a predetermined isoelectric point is deposited in the cavities to provide thereby the particle's isoelectric value.

13 Claims, 5 Drawing Sheets

Protein Sample Behavior at pH 10 on Media pI of 8.5

FIG. 4B

Protein Sample Behavior at pH 8.5 on Media pI of 8.5

FIG. 4C

Protein Sample Behavior at pH 7 on Media pI of 8.5

FIG. 4D

Protein Sample Behavior at pH 5 on Media pI of 8.5

MATERIALS, METHODS AND SYSTEMS FOR SEPARATING AND IDENTIFYING PROTEINS FROM MIXTURES

1 CROSS-REFERENCE TO RELATED PATENT APPLICATIONS

This application claims priority to U.S. Provisional Patent Application Nos. 60/553,605 and 60/553,561, both were filed on Mar. 17, 2004, respectively.

2 FIELD AND BACKGROUND OF THE INVENTION 2.1 Field of the Invention

The present invention relates generally to the field of analytical chemistry, and, more particularly, to the separation of components of complex mixtures. Still more particularly, the present invention relates to the separation of substances having defined isoelectric points from mixtures. The present invention has applications in the fields of biochemistry, proteomics, and clinical chemistry.

2.2 Background

Proteomics, the analysis of the set of proteins expressed in a given biological milieu such as cells, tissues, or fluids, has become the next holy grail of biomedical research. Although the genomes of over one hundred fifty species have been cataloged, a truly functional understanding of the difference between diseased and normal operating states of biological systems requires a correlation of the sequence of gene activity with the corresponding profile of expressed proteins. Gene transcription analysis is not sufficient to achieve this correlation, since many genes are expressed indirectly, e.g., through processing by the so-called spliceosome, regulated by so-called interference RNA ("RNAi"), or the expressed proteins are modified by post-translational factors. Thus, a catalog of proteins must be derived directly.

The two most discriminating techniques for separating component proteins from mixtures of proteins are the protein's isoelectric point and molecular mass: it is highly improbable that two different proteins could have exactly the same isoelectric point and the same molecular mass. These parameters have already been used in two-dimensional electrophoresis ("2-DE"), in which proteins in a mixture are separated first by isoelectric point followed by electrophoretic migration through a sodium dodecylsulfate ("SDS") matrix. However, the use of SDS electrophoresis is not considered to be very efficient for the sort of large scale analysis necessary for proteomic or clinical applications.

Mass spectrometry is a much more powerful technique to determine not only mass, but protein identity by correlating a sample's fragmentation pattern with the fragmentation patterns of known proteins. One approach uses a 2-DE separation using a polyacrylamide gel plate and then each single separated spot is removed from the gel and analyzed by mass spectrometry. However, this is unpractical, because it is too laborious to catalog the thousands of proteins expressed in a typical proteome. A more practical approach would avoid separating proteins from a gel matrix.

Cretich, et al., ("Separation of Proteins in a Multicompartment Electrolyzer with Chambers Defined by a Bed of Gel Beads", *Electrophoresis* 24 (2002) 577-581) describes the separation of proteins based on their isoelectric point using a matrix of cross-linked acrylamide and acrylamide monomers known to those of skill in the art under the trade name IMMOBILINE™ (available from Amersham Biosciences, Uppsala, Sweden). However, the mechanical characteristics of the matrix were less than satisfactory, which lead the authors to suggest the use of electrically inert porous beads. But such beads are not described.

Auto-buffering beads using mixtures of monomers has been described for the maintenance of pH at constant levels in a modifiable environment (e.g., vegetable growth). These beads are described in the literature (see, e.g., Righetti, P. G., Chiari, M. and Crippa, L.: "Macroreticulate Buffers: a Novel Approach to pH Control in Living Systems", *J. Biotechnol.* 17 (1991) 169-176; Chiari, M., Pagani, L. and Righetti, P. G.: "Physico-Chemical Properties of Amphoteric, Isoelectric, Macroreticulate Buffers", *J. Biochem. Biophys. Methods* 23 (1991) 115-130; Pompei, R., Lampis, G., Chiari, M. and Righetti, P. G.: "Culture of Eukaryotic Cells with Macroreticulate Buffers: Fermentation of Cellulolytic Fungi", *BioTechniques* 11 (1991) 701-706). They contained, grafted onto the same, neutral polymer backbone, both the buffering ion and the counter ion needed for titrating the buffering ion around its pK value; so as to ensure maximum buffering capacity. Such beads, however, could only be used for buffering cell growth media, and the like. They could not be adopted as ion exchangers, since their very nature of containing both types of groups—both positively and negatively charged—would render the beads useless as protein exchangers.

Thus, a need remains for a medium for separating mixture components on the basis of their pI using a robust material. The present invention meet this and other needs.

3 SUMMARY OF THE INVENTION

The present invention provides materials, methods, apparatuses, and systems for separating components having defined isoelectric points ("pIs") from mixtures comprising such components.

In one aspect, the present invention provides a particle adapted to have a predetermined isoelectric point. The particle comprises a substantially porous particle body having a plurality of cavities extending inwardly from the surface thereof and a substance of predetermined isoelectric point such that said particle maintains a substantially neutral electrostatic charge at a predetermined pH. In some embodiments the substance is deposited in the cavities of the particle. Examples of such substances include polymers, such as polyacrylamides and block copolymers. In another embodiment, the particle's cavities define interior and exterior surfaces and the substance of predetermined isoelectric point is deposited on said interior and exterior surfaces of the particles. Examples of suitable substances for such embodiments can comprise one, two, or more amino acids.

The particles of the invention can also comprise material substantially incapable of producing an electroendoosmotic force, for example, a particle comprising polystyrene or mineral oxides provided in proportions effective to render said particle substantially incapable of producing an electroendoosmotic force. Examples of suitable materials include zirconia, silica, titania, alumina, and mixtures thereof. Further embodiments of such particles include those in which the particles comprises a base material that produces a first electroendoosmotic force and said base material is substantially coated with a substance that produces an electroendoosmotic force that is substantially equal and opposite to said first electroendoosmotic force. Examples of such combinations include particles having a silica base material and a polycationic hydrophilic polymer coating, or particles having a zirconia base material and a polyanionic hydrophilic polymer coating.

In another aspect, the present invention provides an apparatus for separating one or more components having defined isoelectric points from a mixture comprising such components. In one embodiment, the apparatus comprises a container that is adapted to hold particles having a predetermined isoelectric point of the invention as described herein. The container includes first and second ports to allow introduction of the mixture and removal of the eluents following fluid interaction with the particles within the container. In some more specific embodiments, the mixture has a pH value substantially equal to at least one of the predetermined or defined isoelectric points. In still other embodiments, two or more populations of particles as described herein having a substantially neutral average aggregate electroendoosmotic strength are provided in the container.

In yet another aspect, the present invention provides methods for separating one or more components having defined isoelectric points from mixtures comprising such components. In one embodiment, the mixture is contacted with the particles of the invention such that the particles and components are in fluid contact, which particles have a predetermined isoelectric point. In a more specific embodiment, the predetermined isoelectric point of the particle(s) is substantially equal to the defined isoelectric point of at least one component, e.g., a difference (in absolute value) of pI values of less than about 0.5, more specifically less than about 0.1, still more specifically, less than about 0.01, and, yet more specifically less than about 0.001. The pH of the mixture is adjusted to a value substantially equal to the pI of the particles, i.e., the difference between pH and pI in absolute value is less than 0.5, more specifically less than about 0.1, still more specifically, less than about 0.01, and, yet more specifically less than about 0.001.

In still other aspects, the materials, apparatuses, and methods of the invention are combined with additional analytical systems, such as mass spectrographic analyzers, to provide additional analysis of the mixture components isolated as described herein. Such combinations can provide still more detailed descriptions of the components of complex mixtures, such as blood and other bodily fluid components, for use in proteomic analyses for scientific and clinical applications.

These and still other properties and advantages of the invention will be appreciated when the Description below is read in conjunction with the accompanying Figures.

4 BRIEF DESCRIPTION OF THE DRAWINGS

FIGS. 4A-4D illustrate the operation of the particles of the invention.

5 DESCRIPTION OF SOME EMBODIMENTS OF THE INVENTION

The present invention provides novel materials, methods, and apparatus that can be used to separate substances having differing isoelectric points, especially proteins, from mixtures of such substances. The novel materials, methods, and apparatus described herein can be applied to purify substances by chromatographic separation of mixtures based on differences in the isoelectric points ("pI") of the component substances. In addition, the novel materials, methods, and apparatus described herein can be used in combination with additional materials and apparatus to provide additional analytical information about the purified substance. In some embodiments described herein, substance(s) purified in accordance with the invention are subjected to mass spectroscopic analysis, and, in still more particular embodiments, a time-of-flight ("ToF") mass spectrographic analysis, following purification. In some embodiments, the subsequent analysis is effective to identify the purified substance. Thus, the novel materials, methods, and apparatus of the invention can be used to purify proteins from complex mixtures, thus providing important clinical and biochemical information, e.g., for medical and proteomic applications.

5.1 Particles Having Defined Isoelectric and Electroendoosmotic Properties

In one aspect, the present invention provides particles having defined isoelectric and electroendoosmotic properties that are useful for separating mixture components that have defined isoelectric points. Depending on the pH of the medium in which the particles and mixture components interact, there are situations under which some mixture components have a charge complementary (i.e., of opposite sign) to the particles, and other components that have a charge of the same sign as the particles or which do not carry any charge (i.e., they will be neutral when the $pH=pI_{Component}$). The former components will adsorb more strongly to the particle surface than the latter, which will travel through the column without significant interaction. The adsorbed proteins can then be desorbed by either a pH gradient or a salt gradient. Thus, a separation of components is obtained based on component pI.

In one embodiment, the present invention provides a substantially porous particle body having a plurality of cavities extending inwardly from the surface thereof. The particle further comprises a substance of predetermined isoelectric point such that said particle maintains a substantially neutral electrostatic charge at a predetermined pH. In one embodiment, the particles have sizes, mechanical strengths, and buoyancies that are compatible with separating biological materials. In more specific embodiments, the particles are made using materials such as one or more mineral oxides, or, alternatively, a plastic bead that is sufficiently porous so that a polymer as described herein can be introduced inside the particle. Polystyrene is a well known polymer that can be formed into beads having pores for chromatography. Other synthetic polymers that are useful in the present invention are those based on acrylics such as methymethacrylates, porous nylons, porous polyvinyl plastics, and polycarbonates. Still others will be familiar to those having skill in the polymer arts. In still more specific embodiments, the materials comprise one or more mineral oxides including, but not limited to, a trivalent mineral oxide such as: aluminum, gallium, indium, scandium, yttrium, lanthanum, actinium, or a rare earth mineral; or a tetravalent mineral oxide such as titania, zirconia, or hafnia. Examples of suitable porous particle bodies that can be used in the practice of the invention include the porous particle bodies described in U.S. Pat. Nos. 6,613,234; 5,470,463; 5,393,430; and 5,445,732, each of which is incorporated herein by reference in its entirety and for all purposes. Suitable particles are sold under the trade names HYPERD™ and HYPERD™ by Ciphergen Biosystems of Fremont, Calif.

Thus, in one aspect, the present invention provides a method of making composite particles with a predetermined isoelectric point. In one embodiment, the method comprises the steps of: selecting monomers and their quantities to obtain upon polyermization a cross-linked polymer having the predetermined isoelectric point; preparing a solution of the monomers; contacting the monomer solution with particles having porous particle bodies in which the particles bodies are dimensioned to allow fluid entry into the particles; and reacting the monomers under conditions effective to form the polymer having said predetermined isoelectric point within the porous particle bodies to form thereby composite particles with a predetermined isoelectric point. Exemplary teachings can be found in U.S. Pat. Nos. 6,613,234; 5,470,463; 5,393,430; and 5,445,732. In some embodiments, the particles have diameters between about 10 μm and about 200 μm, and, in more specific embodiments, the particles have pore volumes greater than about 40% of the total particle volumes, and, still more specifically, greater than about 50% of the total particle volume. In some embodiments, monomers are selected from the group consisting of: N-acryloylglycine, 4-acrylamidobutyrric acid, 2-morpholinoethylacrylamide, 3-morpholinopropylacrylamide, N,N-dimethylaminoethylacrylamide, N,N-dimethylaminopropylacrylamide. In other embodiments, particles comprise zirconium oxide. In addition, a poration agent can be optionally use as well. For example, one can add a pore-inducing agent such as polyethyleneglycol 6000 at a concentration between about 8% and about 20%. The particles can also optionally be coated with known passivating agents such as described in published US patent application U.S. 2002-0005383 A1.

In some embodiments of the invention, a substance having a predetermined isoelectric point is deposited in said cavities of said particle. More particular embodiments include those in which the substance is a polymer having a predetermined isoelectric point. In still more specific embodiments, the polymer is a polyacrylamide or the polymer is a block copolymer. Such embodiments can be prepared using materials and methods familiar to those having skill in the arts of polymer chemistry and biochemistry. For example, suitable isoelectric substances can be made by combining acrylamide monomers and immobilines in amounts and under conditions that are effective to produce a polymer having a defined isoelectric point. Briefly, as known to those of skill in the art of bioanalytical chemistry and described in U.S. Pat. No. 4,971,670 to Faupel, et al, immobilines are acrylamide derivatives having the general formula:

where R includes a group that provides the characteristic pI. While there are many molecules that are embraced by this description, one collection for creating isoelectric gels is commercialized by Amersham under the trade name IMMOBILINE®. This collection includes the following molecules ("immobilines") having the indicated pI: N-acryloylglycine (pK 3.6); 4-acrylamidobutyrric acid (pK 4.6); 2-morpholinoethyl-acrylamide (pK 6.2); 3-morpholinopropylacrylamide (pK 7.0); N,N-dimethylaminoethylacrylamide (pK 8.5); and N,N-dimethylaminopropylacrylamide (pK 9.3). These monomers are combined and co-polymerized with acrylamide and N,N'-methylenebisacrylamide, or other suitable cross-linking agent, to produce the desired pI specific polymer. Methylacrylamide can be substituted for acrylamide. Compositions of desired pI can be derived by combining immobilines and co-polymerizing agents using available software, such as Doctor pH (available from Amersham, Uppsala, Sweden at www.amersham.com) according to the information provided under the title "Isoelectric membrane formulas for isoprime purification of proteins" at the following URL:

http://www1.amershambiosciences.com/aptrix/
upp00919.nsf/content/E466EDD469D4CF4BC1256A5
E00538B4E?OpenDocument&Path=Catalog&Hometitle=
Catalog&entry=2&newrel&LinkParent=C12
56B810034E9C1-3F2278B4DDBFF6ED41256B8A003011
A6_RelatedLinksNew-
858FD25382BD896AC1256BC100402117&newrel&hidesearchbox=yes&moduleid=40401

Methods for determining the value of pI for various macromolecules are known. Examples of such methods include: Ribeiro J M. Sillero A. 1990 "An algorithm for the computer calculation of the coefficients of a polynomial that allows determination of isoelectric points of proteins and other macromolecules", *Computers in Biology & Medicine* 20(4):235-42; Ribeiro J M. Sillero A., 1991 "A program to calculate the isoelectric point of macromolecules" *Computers in Biology & Medicine* 21(3):131-41; and Sillero A. Ribeiro J M., 1989 "Isoelectric points of proteins: theoretical determination" *Analytical Biochemistry* 179(2):319-25. Such methods can be used to determine the pI value for the polymers described herein.

For example and without limitation, particles having defined isoelectric points in accordance with the present invention can be prepared in accordance with the specific examples provided in Section 6 below. In summary, as illustrated by Example 1 (Section 6.1), aqueous solutions of acrylamide monomers effective to provide a desired pI are combined with the appropriate cross-linking reagents and polymerization catalysts are combined in a slurry with the above-described particles in proportions sufficient to cause polymerization of the acrylamides within the cavities of the particles as described in greater detail in the incorporated '234 and '763 patents to create thereby particles having a defined pI.

In other embodiments, the substance of predetermined isoelectric point is deposited on said interior and exterior surfaces of the particle (i.e., the interior and exterior particle surfaces formed by the interior pore volume of above-described cavities). The deposition can be by chemical bond or other means. Amino acids are useful to provide such surface layers since amino acids have defined isoelectric points. Thus, in some embodiments, the substance comprises an amino acid; and, in more specific embodiments, the substance comprises two or more amino acids. The amino acid can be any of the twenty naturally-occurring amino acids, or the amino acid can be a unnatural amino acid. More specifically, useful amino acids include those among the twenty naturally occurring amino acids having ionizable side chains, including: lysine, arginine, glutamic acid, aspartic acid, serine, cysteine, threonine, tyrosine, asparagines, glutamine. In addition, it will be understood by those of skill in the biochemistry arts that other compounds having defined pI values that can be attached to the interior and exterior particle surfaces as described above can be used with the present invention. Linkers may be used to provide attachment sites on the surface of the particle. Suitable linker chemistry will be familiar to those of skill in the art of surface chemistry.

One example describing the formation of amino acid modifications to particle surfaces in provided in Example 6.6 below. Porous zirconia beads filled with agarose hydrogel are first reacted with sodium hydroxide (NaOH) and allyl bromide ($CH_2CH_2CH_2Br$) to produce particle surfaces having allyloxy groups attached thereon. The allyloxy groups are further brominated to form 3-bromopropyloxy surface linkers that are subsequently reacted with lysine to provide particles having lysine-linked surfaces with a particle pI value of 8.2.

In other embodiments, the above-described particles further produce substantially zero electroendoosmotic force. In some of these embodiments, the particle comprises a material substantially incapable of producing an electroendoosmotic force, and, in more particular embodiments, the material is polystyrene. In other such embodiments, the particles are formed from two or more materials having substantially equal and opposing electroendoosmotic effects to form thereby particles of substantially zero electroendoosmotic force. Examples of these embodiments include particles having mineral oxides provided in proportions effective to render said particle substantially incapable of producing an electroendoosmotic force. Examples of suitable mineral oxides chosen from the group consisting of: zirconia, silica, titania, alumina, and mixtures thereof.

In still other embodiments, the particle comprises a base material that produces a first electroendoosmotic force and said base material is substantially coated with a substance that produces an electroendoosmotic force that is substantially equal and opposite to said first electroendoosmotic force so that said particle produces a substantially zero electroendoosmotic force. Thus, the present invention provides methods and materials for modifying the electroendoosmotic properties of the particles described herein to provide particles having a substantially zero electroendoosmotic force. Examples of suitable particle-coating combinations include particles in which the base material is silica and said substance is a polycationic hydrophilic polymer and particles in which the base material is zirconia and said substance is a polyanionic hydrophilic polymer. In addition, one or more amino acids suitable polymers can be used to provide the desired compensatory surface layer. Polymers used to coat the mineral oxide and therefore reduce the electroendoosmosis level close to zero are light ionic soluble polymers with a complementary charge. For silica-based beads, for instance, the polymer can be an amino-containing polymer such as a DEAE dextran. In practice, the polymer is put in contact with the silica beads for suitable period of time, and the polymer excess is eliminated by an extensive washing with water. Only the required amount of cationic dextran capable to counterbalance the acidic character of silica will remain with the beads. For zirconium oxide, where the overall charge of the material is positive, appropriate polymers are those that weak acids such as carboxyl groups. The amount of coating polymer is to be chosen so that the net charge of the resulting composite material is approximately zero.

In another aspect, the present invention provides methods and materials for ion exchange chromatography. For example without limitation, a person of skill will understand that the charges on the particles of the invention can be controlled by adjusting the pH of the buffer; since, as described above, at any given pH a particle of the invention will have a charge based on its pI. Once the charges on the particles have been established, then one of skill in the protein purification arts can perform ion exchange chromatography using standard methods, e.g., by loading the particles with a sample, capturing proteins on the particles of the invention based on the charge interactions between the particles and proteins, and then eluting the proteins from particles with, e.g., a step- or continuous salt gradient.

In another aspect, the invention provides apparatuses for separating the components of a mixture on the basis of differing isoelectric points of the components. In one embodiment, described with reference to FIG. 1, the invention provides an apparatus 100 comprising a container 102 dimensioned to retain the above-described particles of defined isoelectric point and allow passage of a mixture over and through the particles to effect separation of mixture components on the basis of the isoelectric points of the components. Container 102 includes an inlet 104 dimensioned to allow introduction of the mixture and an outlet 106 to allow exit of mixture components including components separated from the bulk of the mixture. Between inlet 104 and outlet 106 is a separation zone 108 that includes particles 110 in accordance with the invention. Separation zone 108 thus divides apparatus 100 into pre- and post-separation zones 112 and 114 respectively.

Figure 1:
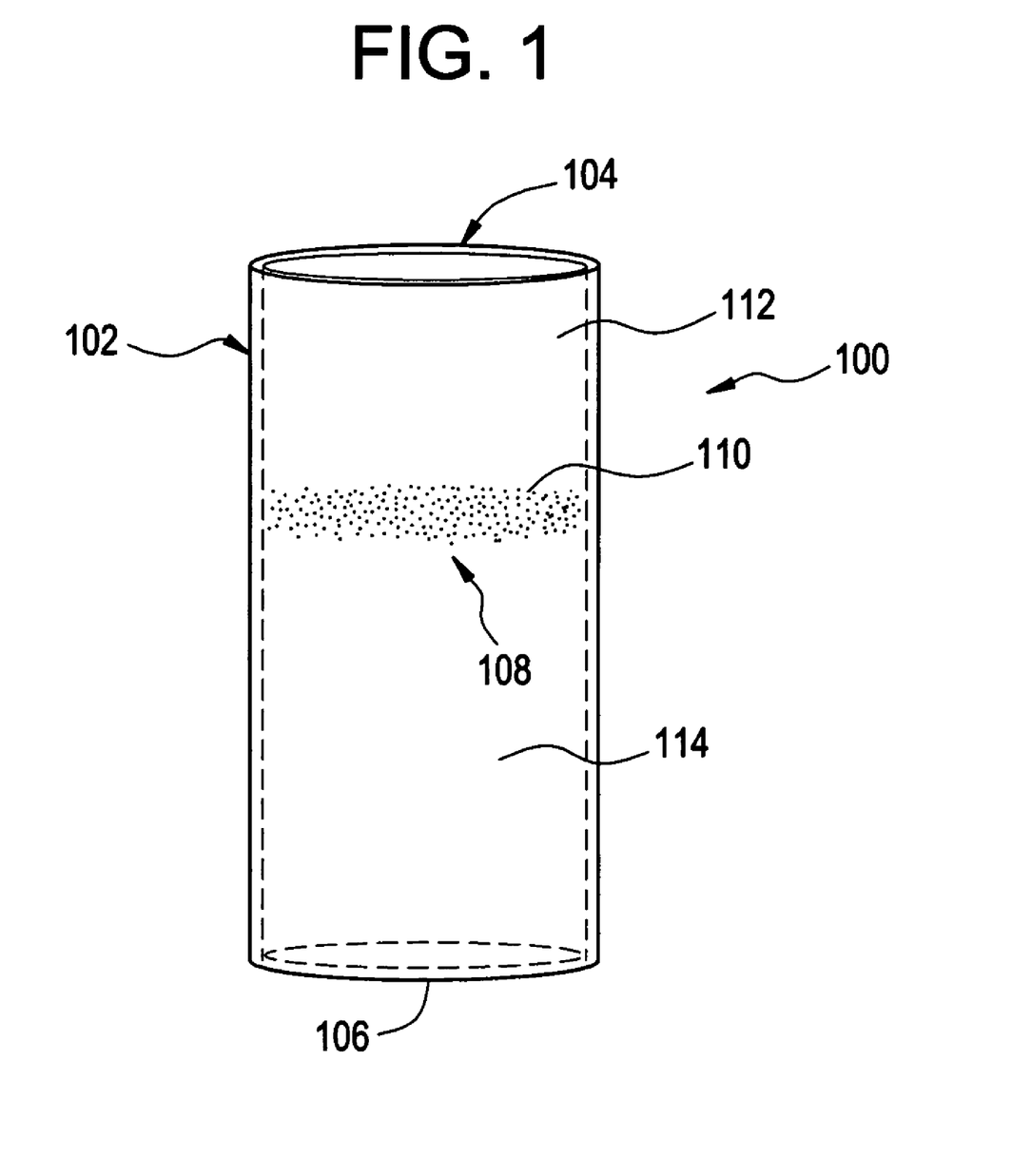
FIG. 1 is a view of an apparatus of the invention including particles of the invention (hidden view) for separating the components of a mixture based on isoelectric points of the components.

The use of the apparatus shown in FIG. 1 to at least partially separate the mixture components will now be described. An unresolved mixture is introduced to zone 112 through inlet 104. An electric potential is created across housing 102 (i.e., between inlet 104 and outlet 106), and the pH of the mixture is adjusted to a value, which can be less than, greater than, or equal to the pI of the particles 110. The mixture is then allowed to pass through separation zone 108 and over the particles 110 to allow at least partial resolution of the components of the mixture as the mixture passes into post-separation zone 114 and exits apparatus 100 through outlet 106 for subsequent collection (e.g., by fractions) or further processing (e.g., by mass spectrographic analysis). The particles will interact according to the principles described above to effect a degree of component separation depending on the pIs of the components and particles.

Figure 2:
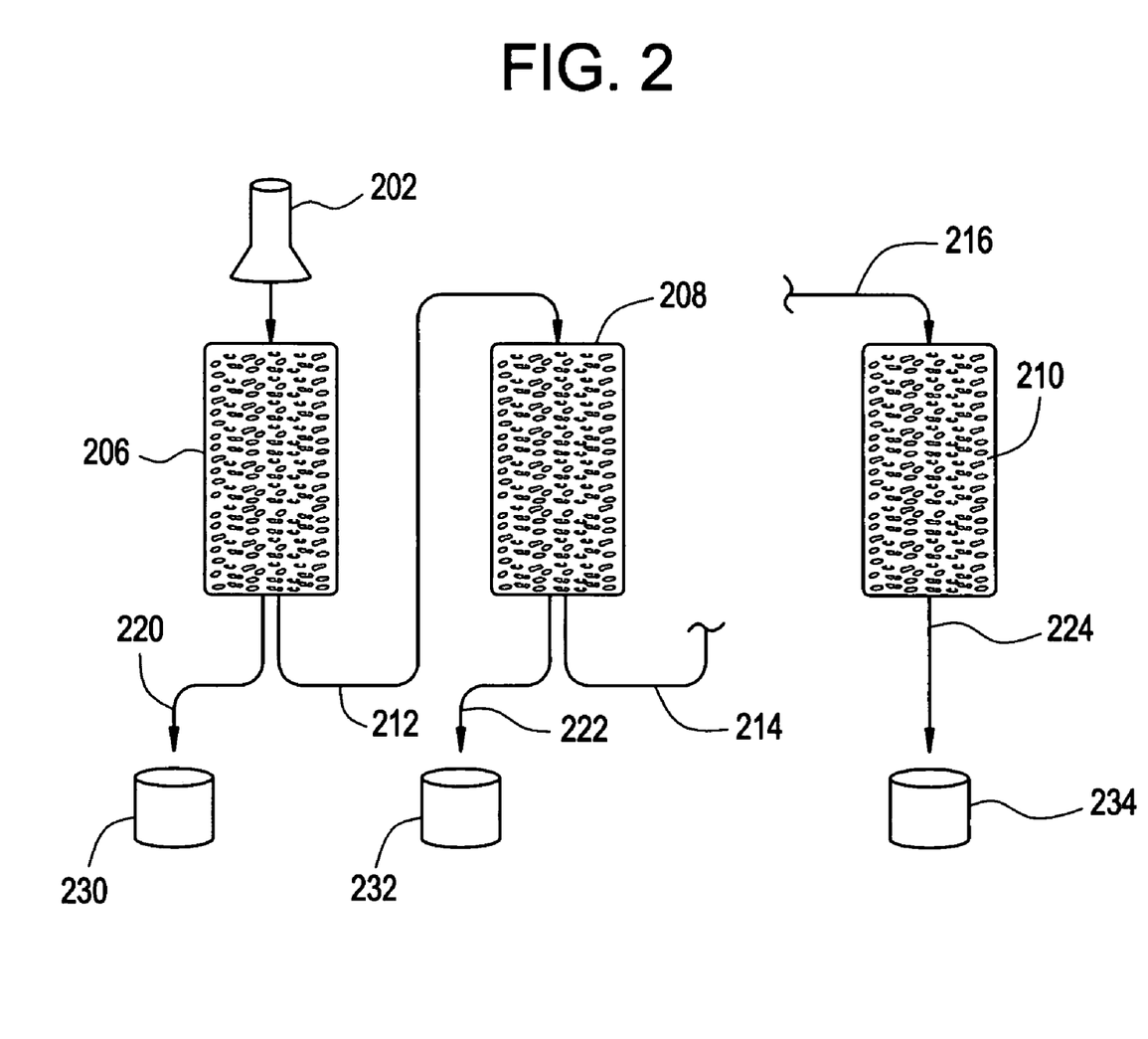
FIG. 2 is a view of an embodiment of the present invention comprising several apparatuses in accordance with present invention coupled in a serial arrangement.

FIG. 2 illustrates another embodiment of the invention at 200. There, a mixture for analysis 202 is introduced to a serial configuration of separation apparatuses shown generally at 204 that includes individual apparatuses 206, 208, and 210, each operating at a different pI value, which are configured and operated as described for apparatus 100 in FIG. 1. The apparatuses 206, 208, and 210, are in fluid communication through connectors 212, 214, and 216 as shown. In addition, an isolate is collected after passage through each individual apparatus as shown at 220, 222, and 224 for collection in receptacles 230, 232, and 234 respectively.

In operation, the mixture to be fractionated is contacted with apparatus 206. The pH of the mixture is adjusted to a desired operating value. If the pH is above the pI of the particles, the particles will have a net negative charge. Conversely when the pH is below the pI of the particles, their net charge is positive. The mixture is contacted with the particles. Any mixture component(s) having an isoelectric point such that they carry an opposite charge to the particles in apparatus 206 will interact with the particles, and therefore elute more slowly, than components having the same charge sign as the particles or components that are neutral at the operating pH. The strongly interacting particles are collected in receptacle 230 and the remaining non-interacting components are transferred to apparatus 208. The pH is for apparatus 208 is adjusted, the mixture is contacted with the particles as just described, and any mixture components that interact strongly with the particles in apparatus 208 are collected in receptacle 232. The remaining material is transferred to the next apparatus and the process described is repeated until the mixture is contacted with the last apparatus 210 whereupon any mixture components that interact strongly with the particles in that apparatus are collected in receptacle 234. The remaining fraction can be separated by different means (e.g., ion-exchange or affinity chromatography) or discarded.

Figure 3:
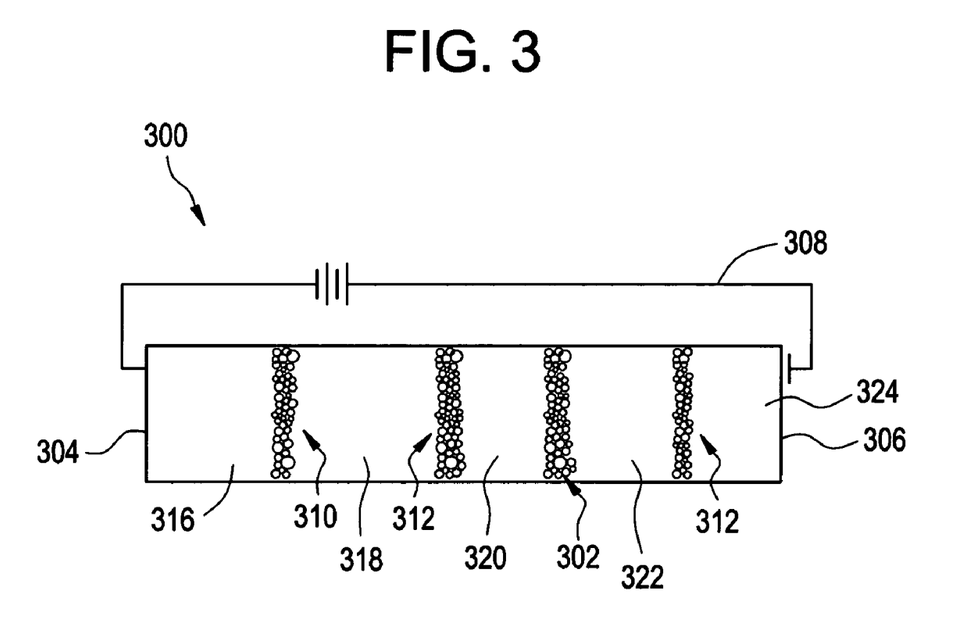
FIG. 3 is a view of a multi-chambered isoelectric focusing device in accordance with the present invention.

FIG. 3 illustrates another embodiment of an apparatus in accordance with the invention at 300. Apparatus 300 includes a substantially hollow housing 302 which includes inlet and outlet 304 and 306 respectively. A means for providing an electrical potential across the length of housing 302 is shown generally at 308. The interior of housing 302 includes separation regions 310, 312, and 314, each of which separation regions comprises particles as described herein wherein the particles of each separation region have a different pI. The separation regions 310, 312, and 314 further divide housing 302 into chambers 316, 318, 320, 322, and 324 respectively. In operation, identical mixtures of components having different isoelectric points is introduced to chambers 316-324 and the pH of each the mixture is adjusted to a different predetermined value. The voltage is applied, and the resulting fractions collected for further analysis.

Figure 4A:
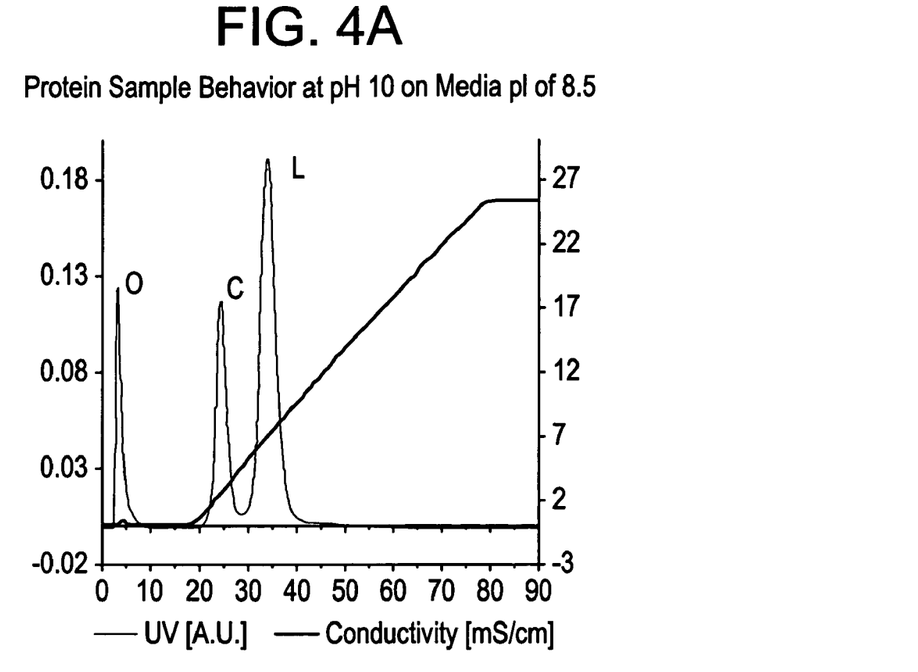
FIG. 4A illustrates the order of elution of ovalbumin ("O"), cytochrome c ("C"), and lysozyme ("L") using particles of the invention having a pI value of 8.5 at a pH of 10.0.

A more detailed description of the operation of the invention is provided with reference to FIGS. 4A-4D. Particles of the invention, having a given isoelectric point (pI=8.5) are prepared as described in Example 6.1. Thus, the particles will be neutral at a pH of 8.5. A sample including ovalbumin (pI=4.5), cytochrome c (pI=10.5), and lysozyme (pI=11.5) is introduced to the particles at one of several pH values, and the mixture is eluted at pH values of 10.0, 8.0, 7.0, and 5.0 with the results shown in FIGS. 4A-4D respectively. Referring now to FIG. 4A, at a pH of 10.0 the particles will carry a net negative charge as will the ovalbumin ("O"). Thus, the ovalbumin will elute first. The cytochrome c ("C") will carry a small positive charge at this pH (a value close to the pI of cytochrome c), and therefore the cytochrome c will interact somewhat with the particles, but not as strongly as the lysozyme ("L"), which will retain a stronger positive charge (pI>pH). These species will thus elute more slowly than the ovalbumin. Thus, FIG. 4A shows the expected separation and order of elution.

Figure 4B:
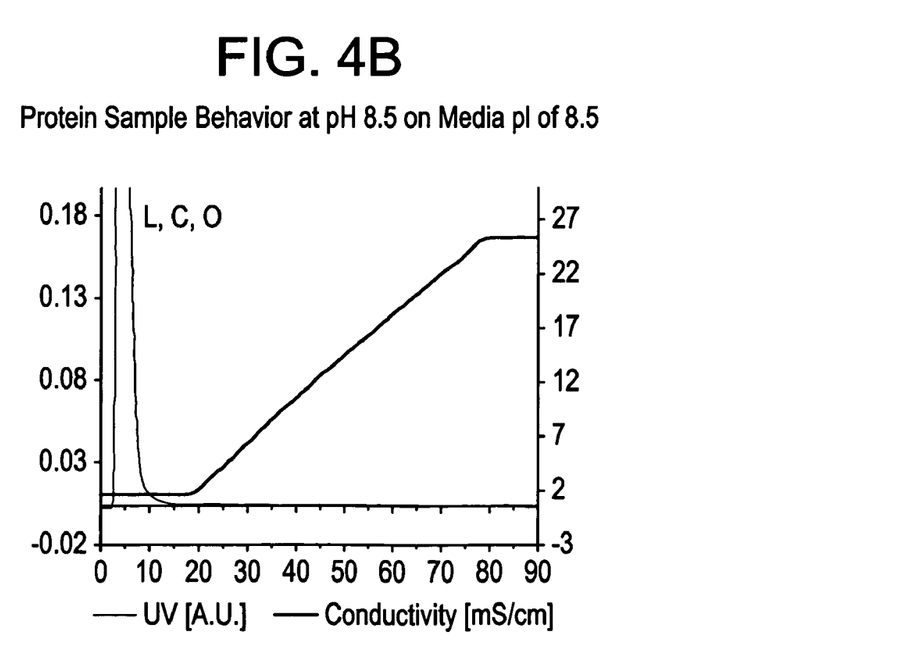
FIG. 4B illustrates the order of elution of ovalbumin ("O"), cytochrome c ("C"), and lysozyme ("L") using particles of the invention having a pI value of 8.5 at a pH of 8.0.
Figure 4C:
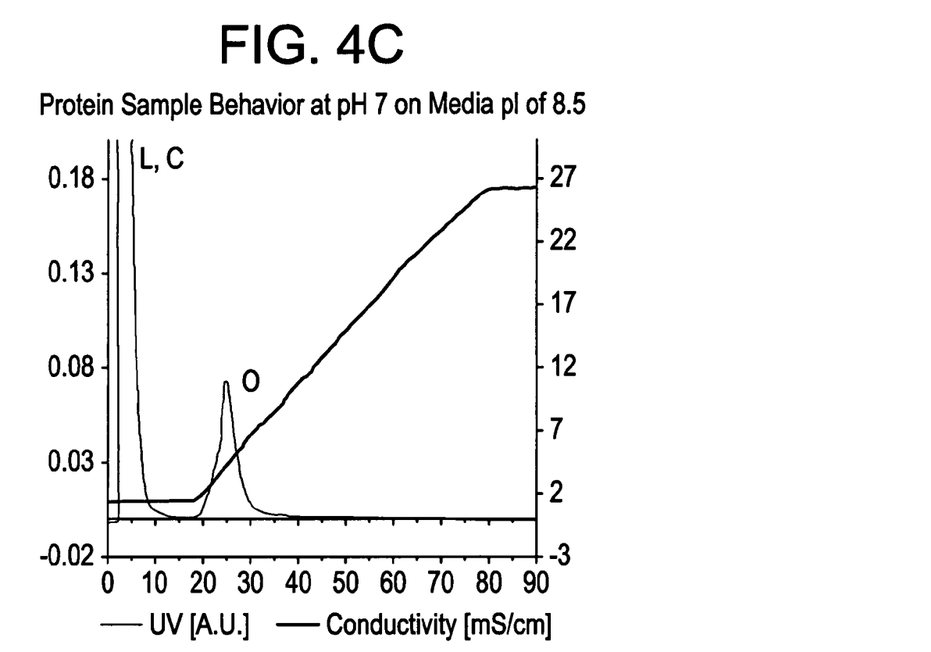
FIG. 4C illustrates the order of elution of ovalbumin ("O"), cytochrome c ("C"), and lysozyme ("L") using particles of the invention having a pI value of 8.5 at a pH of 7.0.
Figure 4D:
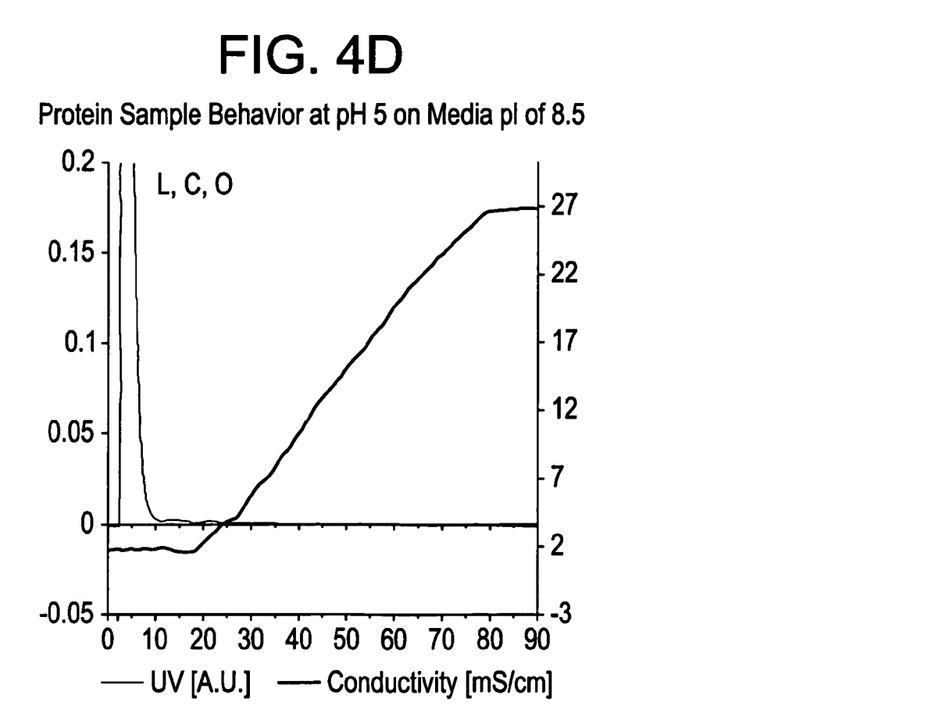
FIG. 4D illustrates the order of elution of ovalbumin ("O"), cytochrome c ("C"), and lysozyme ("L") using particles of the invention having a pI value of 8.5 at a pH of 5.0.

FIG. 4B shows the results of operating at a pH of 8.0, which is close to the pI of the particles. Under such conditions the particles are substantially neutral, and the ovalbumin, cytochrome c, and lysozyme elute together, since there is no interaction with the particles. However, as shown in FIG. 4C, when the pH is 7.0 the particles, as well as the cytochrome c and lysozyme are positively charged while the ovalbumin retains a negative charge. Thus, under these conditions the cytochrome c and lysozyme elute together before the ovalbumin, which will have an electrostatic interaction with the particles. Finally, as shown in FIG. 4D, when the pH approximates the pI of the ovalbumin all of the components will elute together again, since they will have either the same charge as the particles (cytochrom c, lysozyme) or be substantially neutral (ovalbumin).

6 EXAMPLES 6.1 Example 1: Preparation of Zirconium Oxide Isoelectric Beads of pI 8.5

A solution of acrylamide monomers in water was prepared as follows. A first solution was made by combining 2.00 mL of water to 171.00 microliters (μL) of a solution containing 4-acrylamidobutyric acid (0.2 molar (M) concentration), 600 μL of 2-morpholinoethylacrylamide (0.2 M concentration), 475 μL of 3-morpholinopropylacrylamide (0.2 M concentration), 190 μL of N,N-dimethylaminoethylacrylamide (0.2 M concentration), and 64 μL of N,N-dimethylaminopropylacrylamide (0.2 M concentration). The first solution of monomers was then added to a second solution containing three milliliters (3.00 mL) of deionized water, 111.00 μL of 1 M acetic acid. To the combined first and second solutions was added 3.33 mL of a third solution of 28.8 grams (g) of acrylamide and 1.2 g of N,N'-methylenebisacrylamide in 100 mL of water.

To the combined first, second, and third solutions, 4.00 milligrams (mg) of ammonium persulfate and 5.00 μL of N,N,N',N'-tetramethylethylenediamine were added and the resulting combination mixed rapidly at a temperature of 4° C.-6° C.

The resulting solution of monomers and polymerization catalysts was mixed together with solid, porous beads of dextran-passivated silica, in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 8.5.

6.2 Example 2: Preparation of Zirconium Oxide Isoelectric Beads of pI 5.0

A first solution was prepared by adding 2 ml of water to 310 μL of a solution containing N-acryloylglycine (0.2 M concentration), 229 μL of 4-acrylamidobutyric acid (0.2 M concentration), 235 μL of 2-morpholinoethylacrylamide (0.2 M concentration), 65 μL of 3-morpholinopropylacrylamide (0.2 M concentration), and 190 μL of N,N-dimethylaminopropylacrylamide (0.2 M concentration). The first solution of monomers was added to a second solution containing 3.6 mL of deionized water and 47 μL of 1 M tris-hydroxymethylaminomethane. The combined first and second solutions were then combined with 3.33 mL of a third solution containing 28.8 g of acrylamide and 1.2 g of N,N'-methylenebisacrylamide in 100 mL of water.

The three combined solutions were added with 4 mg of ammonium persulfate and 5 μL of N,N,N',N'-tetramethylethylenediamine and mixed rapidly at a temperature of between 4° C. and 8° C.

The resulting solution of monomers and polymerization catalysts was mixed together with solid, porous beads of dextran-passivated zirconium oxide, sold commercially under the trade name HYPERZ™ by Ciphergen Biosystems, Inc. (Fremont, Calif.), in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 5.0

6.3 Example 3: Preparation of Zirconium Oxide Isoelectric Beads of pI 7.0 (Low Charge)

A first solution of acrylamide monomers was prepared by combining 2 ml of water with: 75 µL of solution of N-acryloylglycine (0.2 M concentration), 475 µL of 4-acrylamidobutyric acid (0.2 M concentration), with 208 µL of 2-morpholinoethylacrylamide (0.2 M concentration), with 106 µL of 3-morpholinopropylacrylamide (0.2 M concentration), 294 µL of N,N-dimethylaminoethylacrylamide (0.2 M concentration), and 177 µL of N,N-dimethylaminopropylacrylamide (0.2 M concentration). The first solution of monomers is added to a second solution of 3.30 mL of deionized water and 13 µL of 1 M acetic acid. The combined solutions are then mixed with 3.33 mL of a third solution that included 28.8 g of acrylamide and 1.2 g of N,N'-methymenebisacrylamide in 100 mL of water. The resulting mixture was then combined with a fourth solution containing 4 mg of ammonium persulfate and 5 µL of N,N,N',N'-tetramethylethylenediamine and mixed rapidly at a temperature between 4° C. and 6° C.

The resulting solution of monomers and polymerization catalysts was mixed together with solid, porous beads of dextran-passivated zirconium oxide, sold commercially under the trade name HYPERZ™ by Ciphergen Biosystems, Inc. (Fremont, Calif.), in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 7.0

6.4 Example 4: Preparation of Zirconium Oxide Isoelectric Beads of pI 7.0 (High Charge)

A first solution of acrylamide monomers in water was prepared by combining 10 mL of water with: 175 mg of solution of N-acryloylglycine, 1.34 g of 4-acrylamidobutyric acid, 690 mg of 2-morpholinoethylacrylamide, 380 mg of 3-morpholinopropylacrylamide, 750 µL of N,N-dimethylaminoethylacrylamide, and 500 mg of N,N-dimethylaminopropylacrylamide. The pI of the solution was adjusted to 7.0 with 1 M acetic acid and then 150 mg of N,N'-methymenebisacrylamide and 1.5 g of acrylamide were added to the solution. The volume of the mixture was then adjusted to 30 mL with deionized water, and with 12 mg of ammonium persulfate and 15 µL of N,N,N',N'-tetramethylethylenediamine were added and the combination mixed rapidly at 4° C.-6° C.

The resulting solution of monomers and polymerization catalysts was mixed together with solid, porous beads of dextran-passivated zirconium oxide, sold commercially under the trade name HYPERZ™ by Ciphergen Biosystems, Inc. (Fremont, Calif.), in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 7.0

6.5 Example 5: Preparation of Silicon Oxide Isoelectric Beads of pI 7.0

A first solution of acrylamide monomers in water was prepared by mixing 2 mL of water with 75 µL of solution of N-acryloylglycine (0.2 M concentration), with 475 µL of 4-acrylamidobutyric acid (0.2 M concentration), 208 µL of 2-morpholinoethylacrylamide (0.2 M concentration), 106 µL of 3-morpholinopropylacrylamide (0.2 M concentration), 294 µL of N,N-dimethylaminoethylacrylamide (0.2 M concentration), 177 µL of N,N-dimethylaminopropylacrylamide (0.2 M concentration). The resulting solution of monomers was combined with a second solution made from 3.3 mL deionized water, 13 µL of 1 M acetic acid; and 3.3 mL of a third solution containing 28.8 g of acrylamide and 1.2 g of N,N-methylenebisacrylamide in 100 mL of water. To the resulting solution was added 4 mg of ammonium persulfate and 5 µL of N,N,N',N'-tetramethylethylenediamine and mixed rapidly at 4° C.-6° C.

The resulting solution of monomers and polymerization catalysts was mixed together with solid, porous beads of dextran-passivated silica in an amount sufficient for the porous volumes of the beads to adsorb substantially of the liquid solution, in an amount sufficient for the porous volumes of the beads to absorb substantially all of the liquid solution. The beads were purged of oxygen under vacuum and placed under a nitrogen atmosphere. The mixture was then heated under nitrogen atmosphere at 50° C. for two hours. The beads were then washed extensively with water to remove non-copolymerized materials and by-products. The washed beads were then characterized by a titration curve and a frontal analysis was used to determine the number of charged groups. The resulting composite beads were confirmed to have a pI of 7.0

6.6 Example 6: Preparation of Isoelectric Beads From Lysine

About 100 g of agarose-zirconia composite beads were mixed with 50 mL of 0.5 M an aqueous sodium hydroxide solution at room temperature. Under shaking, 4 mL of allylbromide (available from Sigma-Aldrich Corp. of St. Louis, Mo.) were added and agitation was continued for about twelve hours (overnight). The allylated beads were then separated by filtration and extensively washed with deionized water, drained, and mixed with 50 mL of deionized water at room temperature and under agitation. Five grams of N-bromosuccinimide (available from Sigma-Aldrich Corp. of St. Louis, Mo.) were added to the suspension, and, after about five minutes, 8.3 g of potassium bromide (Sigma-Aldrich) were also added to the agitated mixture. The pI of the suspension was decreased to a value between 3.7 and 3.9 and maintained in that range of values for sixty minutes. The resulting brominated zirconia beads were then collected by filtration and washed extensively with water and re-suspended in 50 mL deionized water. To this suspension, four grams of L-lysine were added; and the pI of the suspension was immediately adjusted to a value between 9 and 10 and maintained for about two hours at room temperature. The desired zirconia beads supporting covalently attached lysine were washed extensively with water to eliminate any non-reacted material and by-products. The beads were characterized by a titration curve and by the number of charged groups and determined to have an isoelectric point of 8.2.

What is claimed:

1. A particle for use in isolating components from a mixture on the basis of isoelectric point, said particle comprising:

(a) a porous particle body having a plurality of cavities extending inwardly from the surface thereof, wherein said porous particle body comprises a base material that produces a first electroendoosmotic force;

(b) a passivating layer coating said porous particle body, wherein said passivating layer produces a second electroendoosmotic force, and wherein said second electroendoosmotic force is equal and opposite to said first electroendoosmotic force, such that said coated porous particle body thereby produces zero electroendoosmotic force;

(c) a substance deposited within said plurality of cavities, wherein said substance has a predetermined isoelectric point and thereby provides said particle with a predetermined isoelectric value.

2. The particle of claim 1, wherein said substance is a polymer.

3. The particle of claim 2, wherein said polymer is a polyacrylamide.

4. The particle of claim 2, wherein said polymer is a block copolymer.

5. The particle of claim 1, wherein said substance comprises an amino acid.

6. The particle of claim 5, wherein said substance comprises two or more amino acids.

7. The particle of claim 1, wherein said base material comprises a mineral oxide.

8. The particle of claim 7, wherein said mineral oxides is a member selected from: zirconia, silica, titania, alumina, and mixtures thereof.

9. The particle of claim 1, wherein said base material is silica and said passivating layer comprises a polycationic hydrophilic polymer.

10. The particle of claim 1, wherein said base material is zirconia and said passivating layer comprises a polyanionic hydrophilic polymer.

11. An apparatus for separating a component having a defined isoelectric point from a mixture having two or more constituents including such component, said apparatus comprising:

(a) a container adapted to hold particles having a predetermined isoelectric value as described in claim 1;

(b) a first port adapted for introduction of said mixture into said container to bring said mixture and said particles in interacting fluid contact, and (c) a second port for removal of non-interacting constituents of said mixture from said apparatus.

12. The apparatus of claim 11 wherein said apparatus further comprises a means for providing an electrical potential between said first port and said second port.

13. A method for separating a component having a defined isoelectric point from a mixture including such component, said method comprising:

(a) introducing said mixture to particles having a predetermined isoelectric point as described in claim 1, said predetermined isoelectric point being substantially equal to the isoelectric point of said component, to place thereby said particles in fluid contact with said component; and, (b) adjusting the pH of said mixture to a value substantially identical to the isoelectric point of said particles to isolate said component from other components of said mixture.

* * * * *